(12) United States Patent
Onuma

(10) Patent No.: US 7,763,755 B2
(45) Date of Patent: Jul. 27, 2010

(54) METHOD FOR PRODUCING DIALKYLHYDROPEROXYBENZENES

(75) Inventor: Mitsuru Onuma, Chiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/279,132

(22) PCT Filed: Feb. 14, 2007

(86) PCT No.: PCT/JP2007/053123

§ 371 (c)(1), (2), (4) Date: Aug. 12, 2008

(87) PCT Pub. No.: WO2007/094504

PCT Pub. Date: Aug. 23, 2007

(65) Prior Publication Data

US 2009/0203943 A1 Aug. 13, 2009

(30) Foreign Application Priority Data

Feb. 16, 2006 (JP) .............................. 2006-039066

(51) Int. Cl.
*C07C 407/00* (2006.01)
(52) U.S. Cl. ..................... 568/571; 568/572; 568/573
(58) Field of Classification Search ................ 568/571, 568/572, 573
See application file for complete search history.

(56) References Cited

U.S. PATENT DOCUMENTS 4,080,386 A * 3/1978 Collins et al. ............... 568/565
4,237,319 A * 12/1980 Nambu et al. .............. 568/571

FOREIGN PATENT DOCUMENTS

| JP | 44-15771 B1 | 7/1969 |
| JP | 63-218656 A | 9/1988 |
| JP | 2000-302752 A | 10/2000 |
| JP | 2002-322146 A | 11/2002 |

* cited by examiner

*Primary Examiner*—Sikarl A Witherspoon
(74) *Attorney, Agent, or Firm*—Sughrue Mion, PLLC

(57) ABSTRACT

To provide a method for producing dialkylhydroperoxybenzene by liquid-phase oxidation of dialkylbenzene, wherein the method comprises the following steps, Oxidation step: a step of obtaining a oxidation reaction liquid having pH of 9 to 12, which contains dialkylhydroperoxybenzene, unreacted dialkylbenzene, and by-produced hydroperoxybenzenes by subjecting an oxidation raw material solution containing dialkylbenzene to oxidation reaction, Aqueous solution extracting step: a step of extracting the oxidation reaction liquid with an alkaline aqueous solution to obtain a water layer mainly containing dialkylhydroperoxybenzene and by-produced hydroperoxybenzenes, and an oil layer mainly containing dialkylbenzene, and Recycle step: a step of recycling and feeding at least a part of the oil layer obtained in the aqueous solution extracting step to the oxidation step, wherein the oxidation step comprises two or more reaction sections of a first section and subsequent sections arranged in series, and the temperature of the first reaction section is set to be higher than an average temperature of the whole reaction sections by 2.5° C. or more.

6 Claims, No Drawings

METHOD FOR PRODUCING DIALKYLHYDROPEROXYBENZENES

TECHNICAL FIELD

The present invention relates to a method for producing dialkylhydroperoxybenzene. More particularly, the present invention relates to a method for producing dialkylhydroperoxybenzene in which dialkylbenzene is oxidized so as to be converted to dialkylhydroperoxybenzene. The method has an excellent characteristics which can produce dialkylhydroperoxybenzene with high selectivity.

BACKGROUND ART

As a method for producing dialkylhydroperoxybenzene by subjecting an oxidation raw material solution containing dialkylbenzene to oxidation reaction, a method for producing 1,3-di-(2-hydroperoxy-2-propyl)benzene is disclosed, for example, in unexamined Japanese Patent Publication No. 2002-322146 as a typical example. In this method, in addition to 1,3-di-(2-hydroperoxy-2-propyl)benzene (hereinafter, referred to as DHPO), the oxidation reaction liquid contains 3-(2-hydroxy-2-propyl)-1-(2-hydroperoxy-2-propyl)benzene (hereinafter, referred to as CHPO), 3-isopropyl-1-(2-hydroperoxy-2-propyl)benzene (hereinafter, referred to as MHPO), unreacted 1,3-diisopropylbenzene (hereinafter, referred to MDC), and by-produced 1,3-di-(2-hydroxy-2-propyl)benzene (hereinafter, referred to as DCA). The oxidation reaction liquid is subjected to extraction using an alkali aqueous solution such as a sodium hydroxide aqueous solution so as to obtain a water layer mainly containing DHPO and CHPO and an oil layer mainly containing MHPO, MDC, and DCA. A part of the oil layer is ordinarily recycled and fed to an oxidation step as a recycled oil in order to recover MHPO and MDC. However, in a conventional technique, the recycled oil contains an extracting agent component such as alkali used in the aqueous solution extracting step, and this alkaline component is fed to the oxidation step with the recycled oil. The alkaline component promotes generations of CHPO and DCA, and reduces a generation of DHPO in the oxidation step. Thus, the yield of DHPO is hardly improved.

Further, the above-described method cannot increase the amount of the recycled oil, and thus cannot keep high MDC concentration in a raw material to be recycled.

Furthermore, Unexamined Japanese Patent Publication No. S59-82327 discloses a technique in which the alkaline component in the recycled oil is washed so as to control pH in an oxidation reactor. However, since pH in the oxidation reactor is kept within the range of 7 to 7.5 in this technique, the amount of the recycled oil cannot be increased. Thus, this technique cannot keep high MDC concentration in a raw material to be recycled.

DISCLOSURE OF THE INVENTION

In view of the above circumstances, an object of the present invention is to provide a method for producing dialkylhydroperoxybenzene, which includes dividing an oxidation step into two or more reaction sections, setting a temperature of a first reaction section to be higher than an average temperature of the whole reaction sections by a specific temperature value or more, and thereby enabling to produce dialkylperoxybenzene with high yield.

Further, an object of the present invention is to provide a method for producing dialkylhydroperoxybenzene, which includes: extracting and separating a valuable component in the oxidation reaction liquid obtained in an oxidation reaction step in an aqueous solution extracting step; recycling at least a part of an obtained oil layer mainly containing dialkylbenzene, and subjecting it to oxidation reaction as a raw material solution. The method for producing dialkylhydroperoxybenzene solves a problem of the conventional technique that the yield of dialkylhydroperoxybenzene is hardly improved due to the influence from an alkaline component used in the aqueous solution extracting step contained in the oil layer. Thus, dialkylhydroperoxybenzene can be produced with high yield.

That is, the present invention is a method for producing dialkylhydroperoxybenzene by liquid-phase oxidation of dialkylbenzene includes the following steps.

Oxidation step: a step of obtaining a oxidation reaction liquid having pH of 9 to 12, which contains dialkylhydroperoxybenzene, unreacted dialkylbenzene, and by-produced hydroperoxybenzenes by subjecting an oxidation raw material solution containing dialkylbenzene to oxidation reaction, Aqueous solution extracting step: a step of extracting the oxidation reaction liquid with an alkaline aqueous solution to obtain a water layer mainly containing dialkylhydroperoxybenzene and by-produced hydroperoxybenzenes, and an oil layer mainly containing dialkylbenzene, and Recycle step: a step of recycling and feeding at least a part of the oil layer obtained in the aqueous solution extracting step to the oxidation step, In this method, the oxidation step comprises two or more reaction sections of a first section and subsequent sections arranged in series, and the temperature of the first reaction section is set to be higher than an average temperature of the whole reaction sections by 2.5° C. or more.

EMBODIMENTS FOR CARRYING OUT THE INVENTION

As dialkylbenzene to be oxidized, benzene having two alkyl groups of 1 to 10 carbon atoms, e.g., metadiethylbenzene, paradiethylbenzene, metadiisopropylbenzene, paradiisopropylbenzene, metadibutylbenzene, and paradibutylbenzene are exemplified. The method of the present invention is properly used for diisopropylbenzene which has isopropyl groups.

Examples to which the present invention is applied will be described below using a process to obtain DHPO from MDC, but the present invention is not limited to this process.

Further, the process to be described is a typical example, and can be properly changed within a range of the present invention. Furthermore, steps in the process are typical steps, and steps within a range of the present invention can be added and removed according to necessity.

The oxidation steps includes subjecting an oxidation raw material solution containing dialkylbenzene to oxidation reaction, and obtaining a oxidation reaction liquid having pH of 9 to 12 and containing dialkylhydroperoxybenzene, unreacted dialkylbenzene, and by-produced hydroperoxybenzenes. A device and a condition to carry out this step are as follows.

An oxidation raw material solution ordinarily, mainly includes MHPO of 20 to 60% by weight, MDC of 10 to 40% by weight, DHPO of 0 to 5% by weight, CHPO of 0 to 10% by weight, and DCA of 0 to 5% by weight. The solution can include a solvent and a compound which does not substantially affect reaction as well. As an oxidizing agent, an oxygen-containing gas such as air or pure oxygen is ordinarily used. Examples of ordinary conditions are: a temperature of 70 to 110° C., a pressure of 0 to 1 MPa (G), and a residence time of 0.01 to 50 hours. Separately, in order to adjust water content, water can be added to the reaction liquid so as to be subjected to oxidation reaction in an emulsion state.

A reaction device used in the oxidation step is a reactor such as a flow type reaction vessel or a reaction column. The reactor needs to have two or more reaction sections in which a first reaction section and reaction sections following the first section are connected in series.

The reaction section in the present invention is a section in which a temperature, a pressure, and a composition are uniform, e.g., a section divided by providing weirs in one reactor, or a section formed with an independent reactor.

The number of these reaction sections is not particularly restricted, but is ordinarily 2 to 10 from the viewpoints of economical efficiency and reaction results. Generally, an oxidation raw material and an oxygen-containing gas are fed to an initial reaction section. However, those can be fed into a part of reaction sections following the initial reaction section by a case.

As for the ordinary concentration of each component in the oxidation reaction liquid obtained in the oxidation step, DHPO is 3 to 30% by weight, CHPO is 0 to 10% by weight, MHPO is 20 to 60% by weight, MDC is 0 to 35% by weight, and DCA is 0 to 5% by weight. The oxidation reaction liquid includes other by-products in addition to these components.

The pH in the oxidation reaction liquid obtained in the oxidation step is 9 to 12, and preferably 9 to 11. When the pH is less than 9, a generation of hydroperoxide is reduced and a device may be corroded on the acidity side. When the pH is more than 12, alkali decomposition of hydroperoxide is promoted so that it is not preferable.

The aqueous solution extracting step includes extracting the oxidation reaction liquid with an alkaline aqueous solution and obtaining a water layer mainly containing dialkylhydroperoxybenzene and by-produced hydroperoxybenzenes and an oil layer mainly containing dialkylbenzene.

The weight ratio of water to oil (water/oil) is ordinarily 0.2 to 5. An aqueous solution is preferably an alkali aqueous solution and alkali is preferably sodium hydroxide. The alkali concentration in the alkali aqueous solution is ordinarily 0.1 to 30% by weight. A general extracting condition is a countercurrent extraction having 1 to 10 stages at a temperature of 0 to 70° C. A device used in the aqueous solution extracting step is a mixer settler or an extraction column.

The recycle step includes recycling and feeding at least a part of the oil layer obtained in the aqueous solution extracting step to the oxidation step (the oil layer to be recycled will be referred to as a recycled oil below). As for the recycled oil, a part or whole of the oil layer obtained in the aqueous solution extracting step is used, but 90 to 100% of the oil layer obtained in the aqueous solution extracting step is generally used.

The recycled oil includes an alkaline component originating in the aqueous solution extracting step. The alkaline component is ordinarily 50 to 3000 ppm by weight as a sodium cation. The pH of the recycled oil is ordinarily 12 to 14.

In the present invention, the oxidation step includes two or more reaction sections. It is necessary that the temperature of the first reaction section is set to be higher by 2.5° C. or more, preferably 3.5° C. or more, than an average temperature of the whole reaction sections. By setting the temperature of the first reaction section as described above, organic acids generated in the first reaction section can be increased. Further, according to the above-described operation, the pH in the first reaction section can be lowered, and thus the amount of the recycled oil to be recycled in the oxidation step can be further increased. In addition, a reaction temperature can be adjusted by a heating operation with warm water using a heat exchanger or a heat removing operation using air or cooling water. When the above-described process is carried out, the above-described problems can be solved. However, the reaction temperature is preferably not more than 20° C. from the viewpoints of energy loss and heat deterioration of hydroperoxide.

Further, the recycled oil can be contacted with wash water before the oxidation step, subjected to liquid separation, and then fed to the oxidation step. Thereby, the higher effect can be obtained.

The wash water can be a water generated in the process, e.g., the separated water after subjecting to liquid separation to water and the oxidation reaction liquid or waste gas condensed water generated in the oxidation step. The wash water can be directly mixed with the recycled oil, or can be used after being diluted with water. The amount of the wash water is 0.01 to 10% by weight with respect to the recycled oil. As for mixing conditions, a temperature is 0 to 80° C., and residence time is 1 to 180 minutes. Further, a device used for the mixing operation is, for example, a line mixer and a mixing vessel.

After the above contact operation, the pH of the recycled oil after subjecting to liquid separation is ordinarily 7 to 13. However, the pH of the recycled oil is preferably adjusted so as to be within a range of 7 to 11 by the amount of the wash water. A device used for the liquid separation is, for example, a settler.

The above-described operation can decrease the influence from the alkaline component contained in the recycled oil and used in the aqueous solution extracting step. Thus, DHPO can be produced with high selectivity.

Further, the operation can increase the amount of the recycled oil recycled in the oxidation step. The recycle operation can decrease the concentration of hydroperoxide in the recycled oil to be recycled in the oxidation step, increase the concentration of MDC, and thus can increase a reaction speed.

EXAMPLES

The present invention will be described by examples.

Example 1

An oxidation step (having three reaction sections) in which three oxidation reaction columns are arranged in series was used. The oxidation reaction is conducted, wherein: an oxidation raw material oil containing recycle components (DHPO: 0.5% by weight, MHPO: 42.0% by weight, MDC: 24.7% by weight, remainders: other components) of 67 parts by volume per one hour was continuously fed to a first reaction column; an air feed amount was controlled so as to have an oxygen concentration at a reactor outlet of 5%; and the reaction conditions were adjusted so that an average temperature of columns was 88.5° C. (a first reactor temperature: 92.0° C., a second reactor temperature: 90.5° C., a third reactor temperature: 83.0° C.), a pressure was 0.3 MPa, a water content was 3 to 4% by weight, and pH was 9 to 11 with a residence time of 10 hours. Fresh MDC of 5 parts by volume per one hour was continuously fed to the oxidation reaction liquid so as to remove separated water. The separated water obtained here was used as wash water. Further, in order to separate DHPO as an objective reaction product from the oxidation reaction liquid after liquid separation, it was extracted with a sodium hydroxide aqueous solution of 7% by weight in an alkali extracting step so as to obtain a sodium hydroxide aqueous solution containing DHPO. The oxidation reaction liquid after extraction with alkali was mixed with the wash water (oxidization separated water) before recycling and feeding it to the oxidation step, and an oil layer after liquid separation was recycled to be used.

Then, in order to separate DHPO as an objective reaction product from the sodium hydroxide aqueous solution containing DHPO, the sodium hydroxide aqueous solution was extracted with methylisobutylketone (hereinafter, referred to as MIBK) in a methylisobutylketone extracting step so as to obtain a MIBK solution containing DHPO. These results are shown in Table 1.

Comparative Example 1

A reaction was carried out by a similar process to that of Example 1 except that an oxidation raw material oil containing recycle components (containing DHPO of 0.2% by weight, MHPO of 38.7% by weight, and MDC of 24.5% by weight) of 72 parts by volume per one hour was continuously fed to an oxidation reactor, and an average reaction temperature was set to be 86.8° C. (a first reactor temperature: 85.5° C., a second reactor temperature: 87.5° C., a third reactor temperature: 87.5° C.). These results are shown in Table 1.

TABLE 1

|  | Example 1 | Comparative Example 1 |
|---|---|---|
| (1) Temperature of a first reactor [° C.] | 92.0 | 85.5 |
| (2) Average temperature of whole rectors [° C.] | 88.5 | 86.8 |
| (1)-(2) [° C.] | 3.5 | −1.3 |
| Production rate of DHPO [Parts by Volume/Hour] | 5.09 | 3.16 |
| DHPO Yield [%] | 74.5 | 66.1 |

DHPO Yield = (DHPO generation mol amount/MDC feeding mol amount)

Clearly from Table 1, Example 1 which is satisfied with conditions of the present invention has more excellent production rate of DHPO and yield than those of Comparative Example 1 which is not satisfied with conditions of the present invention.

INDUSTRIAL APPLICABILITY

In the present invention, an oxidation step is divided to have two or more reaction sections arranged in series, and a temperature of a first reaction section is set to be higher than an average temperature of whole reaction sections by a specific temperature value or more. Thereby, the present invention can provide a method for producing dialkylhydroperoxybenzene with high yield and selectivity.

The invention claimed is:

1. A method for producing dialkylhydroperoxybenzene by liquid-phase oxidation of dialkylbenzene, wherein the method comprises the following steps,
    Oxidation step: a step of obtaining a oxidation reaction liquid having pH of 9 to 12, which contains dialkylhydroperoxybenzene, unreacted dialkylbenzene, and by-produced hydroperoxybenzenes by subjecting an oxidation raw material solution containing dialkylbenzene to oxidation reaction,
    Aqueous solution extracting step: a step of extracting the oxidation reaction liquid with an alkaline aqueous solution to obtain a water layer mainly containing dialkylhydroperoxybenzene and by-produced hydroperoxybenzenes, and an oil layer mainly containing dialkylbenzene, and
    Recycle step: a step of recycling and feeding at least a part of the oil layer obtained in the aqueous solution extracting step to the oxidation step,
wherein the oxidation step comprises two or more reaction sections of a first section and subsequent sections arranged in series, and the temperature of the first reaction section is set to be higher than an average temperature of the whole reaction sections by 2.5° C. or more.

2. The production method according to claim 1, wherein at least a part of the oil layer obtained in the aqueous solution extracting step is contacted to wash water before the oxidation step; and is fed to the oxidation step after liquid separation.

3. The production method according to claim 1, wherein dialkylbenzene is diisopropylbenzene, and dialkylhydroperoxybenzene is diisopropylhydroperoxybenzene.

4. The production method according to claim 3, wherein diisopropylbenzene is metadiisopropylbenzene, and diisopropylhydroperoxybenzene is metadiisopropylhydroperoxybenzene.

5. The production method according to claim 2, wherein wash water is separated liquid water after subjecting the oxidation reaction liquid to liquid separation.

6. The production method according to claim 1, wherein the extracted alkali aqueous solution is a sodium hydroxide aqueous solution.

* * * * *